(12) United States Patent
Dalkara et al.

(10) Patent No.: US 9,597,415 B2
(45) Date of Patent: Mar. 21, 2017

(54) METHODS FOR EXPRESSING A POLYNUCLEOTIDE OF INTEREST IN THE RETINA OF A SUBJECT

(71) Applicants: INSERM (Institut National de la Sante de la Recherche Medicale), Paris (FR); Universite Pierre et Marie Curie (Paris 6), Paris (FR); Centre National de la Recherche Scientifique (CNRS), Paris (FR)

(72) Inventors: Deniz Dalkara, Paris (FR); Alvaro Rendon Fuentes, Paris (FR); Jose Alain Sahel, Paris (FR); Ophelie Vacca, Paris (FR)

(73) Assignees: INSERM (INSTITUTE NATIONAL DE LA SANTE ET DE LA RECHERCHE MEDICALE), Paris (FR); UNIVERSITE PIERRE ET MARIE CURIE (PARIS 6), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/900,350

(22) PCT Filed: Jun. 27, 2014

(86) PCT No.: PCT/EP2014/063676
§ 371 (c)(1),
(2) Date: Dec. 21, 2015

(87) PCT Pub. No.: WO2014/207190
PCT Pub. Date: Dec. 31, 2014

(65) Prior Publication Data
US 2016/0144057 A1 May 26, 2016

(30) Foreign Application Priority Data

Jun. 28, 2013 (EP) .................................... 13305914

(51) Int. Cl.
| | |
|---|---|
| *A61K 48/00* | (2006.01) |
| *C07K 14/47* | (2006.01) |
| *C12N 15/86* | (2006.01) |
| *A61K 9/00* | (2006.01) |
| *A61K 31/713* | (2006.01) |
| *A61K 38/46* | (2006.01) |
| *C12N 7/00* | (2006.01) |
| *C12N 15/113* | (2010.01) |

(52) U.S. Cl.
CPC ........ *A61K 48/0075* (2013.01); *A61K 9/0048* (2013.01); *A61K 31/713* (2013.01); *A61K 38/465* (2013.01); *C07K 14/4703* (2013.01); *C12N 7/00* (2013.01); *C12N 15/113* (2013.01); *C12N 15/86* (2013.01); *C12N 2310/14* (2013.01); *C12N 2320/31* (2013.01); *C12N 2320/32* (2013.01); *C12N 2750/14142* (2013.01); *C12N 2750/14143* (2013.01); *C12N 2750/14171* (2013.01); *C12Y 301/00* (2013.01)

(58) Field of Classification Search
None
See application file for complete search history.

(56) References Cited

U.S. PATENT DOCUMENTS 7,892,809 B2 * 2/2011 Bowles .................. C12N 15/86
435/235.1

FOREIGN PATENT DOCUMENTS

| WO | 2010/000851 A2 | 1/2010 | |
|---|---|---|---|
| WO | 2010/011404 A2 | 1/2010 | |
| WO | 2010/149765 A1 | 12/2010 | |
| WO | WO 2010149765 A1 * | 12/2010 | ......... A01K 67/0275 |
| WO | 2012/145601 A2 | 10/2012 | |

OTHER PUBLICATIONS

Fort et al. Glia 2008;56:597-610.*
Fort et al. Mole Vision 2014;20:1480-90.*
El Mathari et al. Human Mole Genetics 2015;24:3939-47.*
Dalkara et al. Mol Ther. 2009;17: 2096-2102.*
Vacca et al.; "AAV-mediated Gene Delivery in Dp71-null Mouse Model with Compromised Barriers"; GLIA, vol. 62, No. 3, Mar. 31, 2014, pp. 468-476.
Fort et al.; "Dystrophin Protein Dp71 and Retina: a New Phenotype"; ARVA Annual Meeting Abstract Search and Program Planner, vol. 2002, May 5, 2002, p. 661.
Bringmann et al.; "Muller cells in the healthy and diseased retina"; Progress in Retinal and Eye Research, vol. 25, No. 4, Jul. 1, 2006, pp. 397-424.
De Leon et al.; "beta-naphthoflavone represses dystrophin Dp71 expression in hepatic cells"; Biochemica et Biophysica Acta, Mar. 1, 2006, vol. 1759, No. 3-4, pp. 152-158.

* cited by examiner

*Primary Examiner* — Janice Li
(74) *Attorney, Agent, or Firm* — Whitham, Curtis & Cook, P.C.

(57) ABSTRACT

Provided herein are methods for expressing a polynucleotide of interest in the retina of a subject. In particular, a method for expressing a polynucleotide of interest in the retina of a subject comprising the step consisting of injecting into the vitreous an amount of a vector containing the polynucleotide of interest in combination with an amount of an inhibitor of Dp71 expression is provided.

17 Claims, No Drawings

METHODS FOR EXPRESSING A POLYNUCLEOTIDE OF INTEREST IN THE RETINA OF A SUBJECT

FIELD OF THE INVENTION

The present invention relates to methods for expressing a polynucleotide of interest in the retina of a subject.

BACKGROUND OF THE INVENTION

Gene therapy strategies for the treatment of retinal disease have made major advances in recent years, in particular with the use of Adeno-Associated Virus (AAV) vectors. Indeed, AAV vectors are currently among the most frequently used viral vector for gene therapy aimed at inherited retinal disorders and for acquired disorders such as age related macular degeneration or diabetic retinopathy. AAV is regarded as the vector of choice for therapies because of its lack of pathogenicity, long-term gene expression following a single injection, and ability to infect the majority of retinal cells. AAV is a virus composed of a 4.7-kb single-stranded DNA genome enclosed within a 25-nm capsid. The tissue tropism and transduction efficiency of this virus depend on the capsid composition which allows initial receptor attachment, cellular entry, trafficking mechanisms and defines the selectivity for specific cells or tissues. The blood-retinal barrier minimizes systemic dissemination of the virus and the possibility of unwanted systemic side effects following intraocular delivery. Moreover, immune responses following intraocular vector administration are attenuated compared to those following systemic administration. An important limit to such therapy is that for most AAV serotypes intravitreal delivery results in poor retinal transduction, restricted to the inner retinal cells (mostly retinal ganglion cells and some Müller cells). The outer retina (photoreceptors and retinal pigment epithelium) harbor the majority of mutations leading to retinal degeneration. The only way to obtain AAV-mediated gene delivery to these therapeutically important cell-types has been the use of subretinal injection route. However, subretinal injection of AAV needs to make vitrectomy to create a needle hole through the retina and detach the photoreceptors from their supportive retinal pigment epithelium (RPE) with the injection of fluid, causing tissue damage at the site of injection. Three recent clinical trials for the retinal disease type 2 Leber's congenital amaurosis (LCA2) used subretinal injections to deliver AAV that carried the retinal isomerase-encoding gene RPE65 to the RPE; the trial protocol benefited from the atypical pathology of LCA2, which exhibits a loss of photosensitive function without significant structural disruption of retinal layers for many years (Jacobson et al., 2005, Bainbridge et al., 2008, Cideciyan et al., 2008, Maguire et al., 2008, Maguire et al., 2009). In contrast, most retinal degenerative diseases (including retinitis pigmentosa and macular degeneration, which account for half of all retinal degeneration cases) are characterized by the progressive loss of photoreceptor cells and increasingly fragile retinal architecture across the entire retina (Wright et al., 2010, Lin et al., 2009). In such disease states, subretinal surgery can induce mechanical damage, reactive gliosis, and loss of function (Nork et al, 2012). These procedural effects have even been documented in one LCA2 trial, as patients receiving a subretinal injection under the foveal region lost retinal thickness and visual acuity; these results led investigators to conclude that LCA gene therapy is efficacious in the extrafoveal retina but offers no benefit and some risk in treating the fovea (Jacobson et al., 2012). The lack of infection from the vitreous is due to low local concentrations due to diffusion in the vitreous as well as physical barriers to retinal penetration by the viral particles. It has been shown that AAV injected into the vitreous accumulates at the inner limiting membrane (ILM) in area where this membrane is disorganised or, diffuses away from the retina and that a mild digestion of the ILM enhances AAV transduction (Dalkara et al. 2009}. The ILM pose a barrier for the penetration of AAV into the retina from the vitreous in adults but this is the best route for AAV delivery.

SUMMARY OF THE INVENTION

The present invention relates to methods for expressing a polynucleotide of interest in the retina of a subject.

DETAILED DESCRIPTION OF THE INVENTION

The purpose of the inventors was to explore the tropism and the efficiency of AAVs in the Dp71-null mouse model presenting permeable retinal barriers in order to choose the best AAV for a future gene therapy aimed at treating diseases with such symptoms of permeable barriers (such as the blood-retina barrier) and to ensure the safety of the virus infection across leaky BRB. Furthermore, they studied the Müller cells in view of the blood-retinal barrier (BRB) and the inner limiting membrane (ILM) of Dp71-null mice in comparison to wild-type mice. The inventors aimed to understand via AAV infection how these glial cells behave when BRB is compromised. To target the Müller glial cells and thereby the BRB restoration, they used an AAV variant, ShH10-GFP, engineered to target specifically Müller cells (Klimczak et al. 2009). They found that Müller cells are transduced more widely in Dp71-null mice and as glial interactions are altered in Dp71-null mice at the ILM. This leads them to inquire about the integrity of this retinal barrier—the ILM—which has a negative impact on viral transduction after intravitreal administration. The inventors observed on 20 nm-cryosections and on OCT in vivo imaging that the inner retina of Dp71-null mice is significantly thinner than wild-type mice indicating an alteration of the inner retina in the deficient mice. To test if the ILM in Dp71-null mice is really disorganised, they injected AAV5-GFP, an AAV serotype that does not lead to transduction of retinal neurons by intravitreal injection in wild-type mice because of the ILM barrier. They showed that the photoreceptors in Dp71-null mice are largely transduced proving that the ILM in the knockout mouse is altered allowing diffusion of this virus through the retina. Finally, they raised the question of the integrity of the BRB and they checked if AAV can cross the BRB after intravitreal injection of ShH10-GFP, their potential therapeutic vector. The inventors found that no trace of this virus was found in the bloodstream of wild-type mice or in the Dp71-null mice 24, 48 or 72 hours after intravitreal injection of ShH10. Here they demonstrate that, in the Dp71-null mice, the ILM is highly permeable to different AAV serotypes after an intravitreal injection whereas the BRB remains selective for particles such as AAVs.

The present invention relates to a method for expressing a polynucleotide of interest in the retina of a subject comprising the step consisting of injecting into the vitreous an amount of a vector containing the polynucleotide of interest in combination with an amount of an inhibitor of Dp71 expression.

According to the invention, the term "subject" or "subject in need thereof", is intended for a human or non-human mammal. Typically the subject is affected or likely to be affected with a retinal disease.

As used herein the term "retinal disease" refers to a broad class of diseases wherein the functioning of the retina is affected for example due to a damage or degeneration of the photoreceptors; ganglia or optic nerve; or even neovascularization. One skilled in the art can distinguish inherited retinal diseases and acquired retinal diseases. Representative examples of retinal acquired diseases include but are not limited to macular degeneration such as age related macular degeneration, and diabetic retinopathies. Examples of inherited retinal diseases include but are not limited to retinitis pigmentosa, Leber's congenital Amaurosis, X-linked Retinoschisis.

The method of the present invention is particularly relevant for expressing a polynucleotide of interest in the outer retina (photoreceptors and retinal pigment epithelium).

Accordingly, the present invention provides methods for treating, preventing, or, inhibiting retinal diseases, comprising the general step injecting into the vitreous of the subject an amount of a vector containing the polynucleotide of interest in combination with an amount of an inhibitor of Dp71 expression.

A wide variety of diseases of the eye may thus be treated given the teachings provided herein.

For example, the method of the invention is performed in order to treat or prevent macular degeneration. Briefly, the leading cause of visual loss in the elderly is macular degeneration (MD), which has an increasingly important social and economic impact in the United States. As the size of the elderly population increases in this country, age related macular degeneration (AMD) will become a more prevalent cause of blindness than both diabetic retinopathy and glaucoma combined. Although laser treatment has been shown to reduce the risk of extensive macular scarring from the "wet" or neovascular form of the disease, there are currently no effective treatments for the vast majority of patients with MD.

The method of the invention may also be performed in order to treat or prevent an inherited retinal degeneration. One of the most common inherited retinal degenerations is retinitis pigmentosa (RP), which results in the degeneration of photoreceptor cells, and the RPE. Other inherited conditions include Bardet-Biedl syndrome (autosomal recessive); Bassen-Kornzweig syndrome, Best disease, choroidema, gyrate atrophy, Leber congenital amaurosis, Refsun syndrome, Stargardt disease; Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive).

In the context of the invention, the term "treating" or "treatment", as used herein, means reversing, alleviating, inhibiting the progress of, or preventing the disorder or condition to which such term applies, or one or more symptoms of such disorder or condition (i.e., retinal diseases).

One skilled in the art knows, by its knowledge of the scientific literature in his field, which are the polynucleotides that may be more appropriate to treat a specific retinal disease.

In a particular the polynucleotide product is a polypeptide that will enhance the function of a retinal cell, e.g., the function of a rod or cone photoreceptor cell, a retinal ganglion cell, a Müller cell, a bipolar cell, an amacrine cell, a horizontal cell, or a retinal pigmented epithelial cell. Examples of polynucleotides of interest include but are not limited to those encoding for a polypeptide selected from the group consisting of neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) Mol. Ther. 12:659); an Fc fusion protein comprising a soluble Flt polypeptide (see, e.g., Pechan et al. (2009) Gene Ther. 16: 10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-X1); and the like. Other suitable polypeptides include, but are not limited to, glial derived neurotrophic factor (GDNF); fibroblast growth factor 2; neurturin (NTN); ciliary neurotrophic factor (CNTF); nerve growth factor (NGF); neurotrophin-4 (NT4); brain derived neurotrophic factor (BDNF); epidermal growth factor; rhodopsin; X-linked inhibitor of apoptosis; and Sonic hedgehog. Suitable light-responsive opsins include, e.g., a light-responsive opsin as described in U.S. Patent Publication No. 2007/0261127 (e.g., ChR2; Chop2; CaTCh); U.S. Patent Publication No. 2001/0086421; U.S. Patent Publication No. 2010/0015095; and Diester et al. (2011) Nat. Neurosci. 14:387.14:387 or halorhodopsin (e.g. eNpHR) or other light gated ion channel or proton pumps. Suitable polypeptides also include retinoschisin. Suitable polypeptides include, e.g., retinitis pigmentosa GTPase regulator (RGPR)-interacting protein-1 (see, e.g., GenBank Accession Nos. Q96KN7, Q9EPQ2, and Q9GLM3); peripherin-2 (Prph2) (see, e.g., GenBank Accession No. NP_000313; peripherin; a retinal proteinisomerase (RPE65), (see, e.g., GenBank AAC39660; and Morimura et al. (1998) Proc. Natl. Acad. Sci. USA 95:3088); and the like. Suitable polypeptides also include: CHM (choroidermia (Rab escort protein 1)), a polypeptide that, when defective or missing, causes choroideremia (see, e.g., Donnelly et al. (1994) Hum. Mol. Genet. 3: 1017; and van Bokhoven et al. (1994) Hum. Mol. Genet. 3: 1041); and Crumbs homolog 1 (CRB1), a polypeptide that, when defective or missing, causes Leber congenital amaurosis and retinitis pigmentosa (see, e.g., den Hollander et al. (1999) Nat. Genet. 23:217; and GenBank Accession No. CAM23328). Suitable polypeptides also include polypeptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) Ophthalmology 118: 160-167); cone photoreceptor cGMP-gated cation channel beta-subunit (CNGB3) (see, e.g., Kohl et al. (2005) Eur J Hum Genet. 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) Nature 461(7265):784-787. In a particular embodiment, the polynucleotide of interest may encode for a neurotrophic factor. As used herein, the "neurotrophic factor" is a generic term of proteins having a physiological action such as survival and maintenance of nerve cells, promotion of neuronal differentiation. Examples of neurotrophic factors include but are not limited to bFGF, aFGF, BDNF, CNTF, IL-1beta, NT-3, IGF-II, GDNF, NGF and RdCVF.

In certain circumstances, the polynucleotide product of interest is a site-specific endonuclease that provides for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease (such as TALEnucleases, meganucleases or Zinc finger nucleases) can be targeted to the defective allele and knock out the defective allele. In addition to knocking out a defective allele, a site-specific nuclease can also be used to stimulate homologous recombination with a donor DNA that encodes a functional copy of the protein encoded by the defective allele. Thus, e.g., the method of the invention can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) Nature 475:217. In some embodiments, the vector comprises a polynucleotide that encodes a site-specific endonuclease; and a polynucleotide that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, and the like. Site-specific endonucleases that are suitable for use include, e.g., zinc finger nucleases (ZFNs); and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

In some embodiments, the polynucleotide product is an interfering RNA (RNAi). Typically, suitable RNAi include RNAi that decrease the level of an apoptotic or angiogenic factor in a cell. For example, an RNAi can be an shRNA or siRNA that reduces the level of a polynucleotide product that induces or promotes apoptosis in a cell. Genes whose polynucleotide products induce or promote apoptosis are referred to herein as "pro-apoptotic genes" and the products of those genes (mRNA; protein) are referred to as "pro-apoptotic polynucleotide products." Pro-apoptotic polynucleotide products include, e.g., Bax, Bid, Bak, and Bad polynucleotide products. See, e.g., U.S. Pat. No. 7,846,730. Interfering RNAs could also be against an angiogenic product, for example VEGF (e.g., Cand5; see, e.g., U.S. Patent Publication No. 2011/0143400; U.S. Patent Publication No. 2008/0188437; and Reich et al. (2003) Mol. Vis. 9:210), VEGFR1 (e.g., Sirna-027; see, e.g., Kaiser et al. (2010) Am. J. Ophthalmol. 150:33; and Shen et al. (2006) Gene Ther. 13:225), or VEGFR2 (Kou et al. (2005) Biochem. 44: 15064). See also, U.S. Pat. Nos. 6,649,596, 6,399,586, 5,661,135, 5,639,872, and 5,639,736; and U.S. Pat. Nos. 7,947,659 and 7,919,473.

In one embodiment, the vector containing the polynucleotide of interest is selected from the group consisting of viral gene delivery vectors. Viral gene delivery vectors include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus and AAV vectors. Preferred viral gene delivery vector are rAAV vectors. "AAV" is an abbreviation for adeno-associated virus, and may be used to refer to the virus itself or derivatives thereof. The term covers all serotypes and variants both naturally occurring and engineered forms. The abbreviation "rAAV" refers to recombinant adeno-associated virus, also referred to as a recombinant AAV vector (or "rAAV vector"). The term "AAV" includes but is not limited to AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), and AAV type 8 (AAV-8).) and AAV type 9 (AAV9). The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077 (AAV-1), AF063497 (AAV-1), NC_001401 (AAV-2), AF043303 (AAV-2), NC_001729 (AAV-3), NC_001829 (AAV-4), U89790 (AAV-4), NC_006152 (AAV-5), AF513851 (AAV-7), AF513852 (AAV-8), and NC_006261 (AAV-8). A "rAAV vector" as used herein refers to an AAV vector comprising the polynucleotide of interest (i.e a heterologous polynucleotide) for the genetic transformation of a cell. In general, the rAAV vectors contain 5' and 3' adeno-associated virus inverted terminal repeats (ITRs), and the polynucleotide of interest operatively linked to sequences which regulate its expression in a target cell.

In some embodiments, the vector is a pseudotyped AAV vector. The phrase "pseudotyped AAV vector", herein designates a vector particle comprising a native AAV capsid including an rAAV vector genome and AAV Rep proteins, wherein Cap, Rep and the ITRs of the vector genome come from at least 2 different AAV serotypes. Examples of AAV chimeric vectors include but are not limited to AAV2/5, AAV2/6, and AAV2/8. In some embodiments, the AAV chimeric vector is the AAV2/8 described in U.S. Pat. No. 7,282,199, which is incorporated by reference herein.

In some embodiments, the vector is an engineered AAV vector. In particular, the engineered AAV vector is the SH10 vector as described in Klimczak R R, Koerber J T, Dalkara D, Flannery J G, Schaffer D V. 2009. A novel adeno-associated viral variant for efficient and selective intravitreal transduction of rat Muller cells. PLoS One 4(10):e7467. AAV variant ShH10 is closely related to AAV serotype 6 (AAV6). In some embodiments, the AAV engineered vector has a mutated capsid, in particular a tyrosine mutated capsid. In some embodiments, the AAV engineered vector is the one described in WO2012145601 which is incorporated by reference herein. In some embodiments, the vector is a recombinant adeno-associated virus (rAAV) virion comprising a variant AAV capsid protein, wherein the variant AAV capsid protein comprises an insertion of from about 5 amino acids to about 11 amino acids in the capsid protein GH loop relative to a corresponding parental AAV capsid protein, and wherein the variant capsid protein confers increased infectivity of a retinal cell compared to the infectivity of the retinal cell by an AAV virion comprising the corresponding parental AAV capsid protein. In some embodiments, the vector is the AAV2-7m8 as described in WO2012145601 and Dalkara D, Byrne L C, Klimczak R R, Visel M, Yin L, Merigan W H, Flannery J G, Schaffer D V. In vivo-directed evolution of a new adeno-associated virus for therapeutic outer retinal gene delivery from the vitreous. Sci Transl Med. 2013 Jun. 12; 5(189):189ra76. Other examples include those described in:

- Kay C N, Ryals R C, Aslanidi G V, Min S H, Ruan Q, Sun J, Dyka F M, Kasuga D, Ayala A E, Van Vliet K, Agbandje-McKenna M, Hauswirth W W, Boye S L, Boye S E. Targeting photoreceptors via intravitreal delivery using novel, capsid-mutated AAV vectors. PLoS One. 2013 Apr. 26; 8(4):e62097. doi: 10.1371/journal.pone.0062097.
- Dalkara D, Byrne L C, Lee T, Hoffmann N V, Schaffer D V, Flannery J G. Enhanced gene delivery to the neonatal retina through systemic administration of tyrosine-mutated AAV9. Gene Ther. 2012 February; 19(2):176-81. doi: 10.1038/gt.2011.163. Epub 2011 Oct. 20.
- Petrs-Silva H, Dinculescu A, Li Q, Min S H, Chiodo V, Pang J J, Zhong L, Zolotukhin S, Srivastava A, Lewin A S, Hauswirth W W. High-efficiency transduction of the mouse retina by tyrosine-mutant AAV serotype vectors. Mol Ther. 2009 March; 17(3):463-71.
- Petrs-Silva H, Dinculescu A, Li Q, Deng W T, Pang J J, Min S H, Chiodo V, Neeley A W, Govindasamy L, Bennett A, Agbandje-McKenna M, Zhong L, Li B, Jayandharan G R, Srivastava A, Lewin A S, Hauswirth W W. Novel properties of tyrosine-mutant AAV2 vectors in the mouse retina. Mol Ther. 2011 February; 19(2):293-301. doi: 10.1038/mt.2010.234. Epub 2010 Nov. 2.

The vector may also comprise regulatory sequences allowing expression and, secretion of the encoded protein, such as e.g., a promoter, enhancer, polyadenylation signal, internal ribosome entry sites (IRES), sequences encoding protein transduction domains (PTD), and the like. In this regard, the vector comprises a promoter region, operably linked to the polynucleotide of interest, to cause or improve expression of the protein in infected cells. Such a promoter may be ubiquitous, tissue-specific, strong, weak, regulated, chimeric, inducible, etc., to allow efficient and suitable production of the protein in the infected tissue. The promoter may be homologous to the encoded protein, or heterologous, including cellular, viral, fungal, plant or synthetic promoters. Most preferred promoters for use in the present invention shall be functional in cells or the retina, more preferably in photoreceptor or ganglion cells of the retina or in cells of the RPE. Examples of such regulated promoters include, without limitation, Tet on/off element-containing promoters, rapamycin-inducible promoters and metallothionein promoters. Examples of ubiquitous promoters include viral promoters, particularly the CMV promoter, the RSV promoter, the SV40 promoter, etc. and cellular promoters such as the PGK (phosphoglycerate kinase) promoter. The promoters may also be neurospecific promoters such as the Synapsin or the NSE (Neuron Specific Enolase) promoters (or NRSE (Neuron restrictive silencer element) sequences placed upstream from the ubiquitous PGK promoter), or promoters specific for various retinal cell types such as the RPE65, the VMD2, the Rhodopsin or the cone arrestin promoters. The vector may also comprise target sequences for miRNAs achieving suppression of transgene expression in non-desired cells. For example, suppression of expression in the hematopoietic lineages ("de-targeting") enables stable gene transfer in the transduced cells by reducing the incidence and the extent of the transgene-specific immune response (Brown B D, Nature Medicine 2008). In a particular embodiment, the vector comprises a leader sequence allowing secretion of the encoded protein. Fusion of the polynucleotide of interest with a sequence encoding a secretion signal peptide (usually located at the N-terminal end of secreted polypeptides) will allow the production of the therapeutic protein in a form that can be secreted from the transduced cells. Examples of such signal peptides include the albumin, the β-glucuronidase, the alkaline protease or the fibronectin secretory signal peptides. In a most preferred embodiment, the promoter is specific or functional in cells of the retina, in particular in photoreceptor or ganglion cells of the retina or in the RPE, i.e., allows (preferential) expression of the transgene in said cells. For example, suitable photoreceptor-specific regulatory elements include, e.g., a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9: 1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225).

The doses of vectors may be easily adapted by the skilled artisan, e.g., depending on the disease condition, the subject (for example, according to his weight, metabolism, etc.), the treatment schedule, etc. A preferred effective dose within the context of this invention is a dose allowing an optimal transduction of the cells of the retina (photoreceptor or ganglion cells or cells of the RPE). Typically, from $10^8$ to $10^{12}$ viral genomes (transducing units) are administered per dose in mice, preferably from about $10^9$ to $10^{11}$. Typically, the doses of AAV vectors to be administered in humans may range from $10^8$ to $10^{12}$ viral genomes, most preferably from $10^9$ to $10^{11}$.

The term "Dp71" has its general meaning in the art and refers to the Duchenne Muscular Dystrophy (DMD) gene product 71. Dp71 protein consists of a unique seven-residues N-terminus fused to the cysteine-rich and C-terminal domains of dystrophin (Hugnot, J. P., (1992) Lederfein, D., (1992)). Exemplary native Dp71 amino acid and nucleotide sequences are depicted in table 1:

TABLE 1 isoforms of Dp71 transcript variants

| Isoform | Genebank Accession Number | GenPept database Acce |
| --- | --- | --- |
| Transcript variant Dp71ab, mRNA | NM_004018 | NP_004009 |
| Transcript variant Dp71a, mRNA | NM_004017 | NP_004008 |
| Transcript variant Dp71b, mRNA | NM_004016 | NP_004007 |
| transcript variant Dp71, mRNA | NM_004015 | NP_004006 |

An "inhibitor of Dp71 expression" refers to a natural or synthetic compound that has a biological effect to inhibit or significantly reduce the expression of Dp71.

Inhibitor of the Dp71 expression may consist in a small organic molecule that inhibits the expression of Dp71. In particular, inhibitors of Dp 71 may consist in beta-nataphtoflavone as those described in Bermudez de Leon et al. (2006).

Inhibitors of expression for use in the present invention may be also based on anti-sense oligonucleotide constructs. Anti-sense oligonucleotides, including anti-sense RNA molecules and anti-sense DNA molecules, would act to directly block the translation of Dp71 mRNA by binding thereto and thus preventing protein translation or increasing mRNA degradation, thus decreasing the level of Dp71, and thus activity, in a cell. For example, antisense oligonucleotides of at least about 15 bases and complementary to unique regions of the mRNA transcript sequence encoding Dp71 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. Dp71 gene expression can be reduced by contacting a subject or cell with a small double stranded RNA (dsRNA), or a vector or construct causing the production of a small double stranded RNA, such that Dp71 gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). All or part of the phosphodiester bonds of the siRNAs of the invention are advantageously protected. This protection is generally implemented via the chemical route using methods that are known by art. The phosphodiester bonds can be protected, for example, by a thiol or amine functional group or by a phenyl group. The 5'- and/or 3'-ends of the siRNAs of the invention are also advantageously protected, for example, using the technique described above for protecting the phosphodiester bonds. The siRNAs sequences advantageously comprise at least twelve contiguous dinucleotides or their derivatives. As used herein, the term "siRNA derivatives" with respect to the present nucleic acid sequences refers to a nucleic acid having a percentage of identity of at least 90% with erythropoietin or fragment thereof, preferably of at least 95%, as an example of at least 98%, and more preferably of at least 98%. As used herein, "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid sequences. As used herein, "best alignment" or "optimal alignment", means the alignment for which the determined percentage of identity (see below) is the highest. Sequences comparison between two nucleic acids sequences are usually realized by comparing these sequences that have been previously align according to the best alignment; this comparison is realized on segments of comparison in order to identify and compared the local regions of similarity. The best sequence alignment to perform comparison can be realized, beside by a manual way, by using the global homology algorithm developed by SMITH and WATERMAN (*Ad. App. Math.*, vol. 2, p: 482, 1981), by using the local homology algorithm developped by NEDDLEMAN and WUNSCH (*J. Mol. Biol.*, vol. 48, p: 443, 1970), by using the method of similarities developed by PEARSON and LIPMAN (*Proc. Natl. Acd. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably use BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

One essential feature of the invention is that the antisense oligonucleotide is not delivered in association with a viral vector. Accordingly, the antisense oligonucleotide is injected alone (i.e. "naked") in the vitreous of the patient and use of viral vectors encoding for the inhibitor of Dp71 expression is thus excluded from the scope of the invention. One skilled in the art knows that antisense oligonucleotides are commonly used in clinics for intravitreal injections (e.g. against cytomegalovirus retinal infections immunocompromised patients with Vitravene®, retinal delivery by repeated intravitreal injections).

In some embodiment, the vector containing the polynucleotide of interest and the inhibitor of Dp71 expression are to be used simultaneous or sequentially within a given time. The inhibitor of Dp71 expression can be injected into the vitreous in either order, e.g. the inhibitor of Dp71 expression can be injected first into the vitreous and then the vector containing the polynucleotide of interest can be injected or vice versa.

The present invention also provides a pharmaceutical composition comprising a vector containing the polynucleotide of interest, an inhibitor of Dp71 expression and a pharmaceutically acceptable carrier, diluent, excipient, or buffer. According to the invention, the pharmaceutical composition is compatible for intravitreal injection. In some embodiments, the pharmaceutically acceptable carrier, diluent, excipient, or buffer is suitable for use in a human. Such excipients, carriers, diluents, and buffers include any pharmaceutical agent that can be administered without undue toxicity. Carriers might include cationic lipids, nonionic lipids and polyethylene glycol (PEG) as synthetic vectors to enhance siRNA delivery. siRNA might be contained in the hydrophilic interior of the particle or polyethyleneimine and derivatives can be used to fabricate both linear and branched polymeric delivery agents. Cationic polymers with a linear or branched structure can serve as efficient transfection agents because of their ability to bind and condense nucleic acids into stabilized nanoparticles. Such materials have also been shown to stimulate nonspecific endocytosis as well as endosomal escape necessary to enhance nucleic acid uptake. Cyclodextrin-based delivery agents can also be used to increase siRNA delivery. Pharmaceutically acceptable excipients include, but are not limited to, liquids such as water, saline, glycerol and ethanol.

Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The invention will be further illustrated by the following figures and examples. However, these examples and figures should not be interpreted in any way as limiting the scope of the present invention.

EXAMPLE

AAV Mediated Gene Delivery in Retinal Diseases with Compromised Barriers

Material & Methods

Animals

The Dp71-null mice (Sarig et al. 1999) was a kind gift from Dr David Yaffe and were produced by replacing, via homologous recombination, most of the first and unique exon of Dp71 and of a small part of Dp71 first intron with a sequence encoding a β-gal-neomycine-resistance chimeric protein (β-geo). In this mouse line, Dp71 expression is abolished without interfering with the expression of other products of the DMD (Duchenne Muscular Dystrophy) gene. C57BL/6J mice strain (JANVIER, France) was used as controls for this study. All animals used in this study were cared for and handled according to the ARVO Statement for the Use of Animals in Ophthalmic and Vision Research.

Generation and Purification of AAV Vectors

Recombinant AAVs were produced by the plasmid co-transfection method (Choi et al. 2007a; Choi et al. 2007b), and the resulting lysates were purified via iodixanol gradient ultracentrifugation as previously described. Briefly 40% iodixanol fraction was concentrated and buffer exchanged using Amicon Ultra-15 Centrifugal Filter Units. Vector stocks were then tittered for DNase-resistant vector genomes by real time PCR relative to a standard (Aurnhammer et al. 2012).

Injections

Before vector administration, mice were anesthetized with ketamine (50 mg/kg) xylazine (10 mg/kg Rompum). Pupils were dilated by the ocular instillation of neosynephrine 5% Faure (Europhta) and mydriaticum 0.5% (Théa) eye drops. An ultrafine 30-gauge disposable needle was passed through the sclera, at the equator and next to the limbus, into the vitreous cavity. Injection of 1 µl stock containing 1-4× $10^{11}$ vp, was made with direct observation of the needle in the center of the vitreous cavity. Left eyes were injected and right eyes served as control.

Fundus Photography

Fundus examinations were performed at 7, 14, 21 and 28 days after the intravitreal injection of AAV5 or ShH10 coding GFP under the ubiquitous CAG promoter. Fundus photographs were obtained with a scanning laser ophthalmoscope (SLO) (HRA, Heidelberg, Germany) or a Micron III fundus camera. Mouse pupils were dilated by the application of neosynephrine (5%) and mydriaticum (0.5%) eye drops prior to imaging.

Optical Coherence Tomography

OCT was performed using an SD-OCT system (Bioptigen Inc., Durham, N.C.). Hydration with normal saline was used to preserve corneal clarity. Volume analysis centered on the optic nerve head was performed, using 100 horizontal, raster, and consecutive B-scan lines, each one composed of 1200 A-scans. The volume size was 1.4×0.1 mm either side of the optic nerve. A custom software was used to generate the en face fundus image using reflectance information obtained from the OCT sections (volume intensity projection), so that the point-to-point correlation between OCT and fundus position was possible and accurate.

PCR analysis of Mouse Blood Samples

Genomic DNA from blood samples was extracted using QIAamp® DNA Micro Kit (QIAGEN, Germany) according to the manufacturer's instructions. PCR amplifications of genomic DNA were performed using GoTaq® DNA polymerase (Promega, USA) on a ThermoCycler instrument (Applied Biosystem). PCR primers were designed using Primer3 software.

Immunochemistry

One month after vector injection, enucleated eyes were dissected to remove lens and cornea, and fixed by immersion in 4% paraformaldehyde for 1 hour. Fixed eyes were cryo-protected in 30% sucrose, frozen and embedded in Cryomatrix (Thermo Shandon). 10 µm-cryosections were cut and mounted on SuperFrost/Plus slides (Microm). Sections were permeabilized for 10 minutes with 0.1% Triton X100 in PBS (Phosphate Buffer Saline) and blocked for 1 hour with 1% bovine serum albumin, 0.1% Tween 20 in PBS. For retinal flatmounts, enucleated eyes were immersion fixed in 4% paraformaldehyde for 10 minutes. Retinas were separated from the RPE and sclera by cutting around the ora serrata and cutting the optic nerve. For agarose sections, fixed retinas were rinsed in PBS, embedded in warm 5% agarose (type XI, Sigma) and sectioned at 100 µm with a vibratome (Leica, Allendale, N.J.). Sections were then incubated with primary antibodies diluted 1:500 at 4° C. overnight. After several washes with PBS, secondary antibodies (Interchim, France) coupled to Alexa fluor (Invitrogen, France) were used diluted 1:800 for 1 hour at room temperature. Retinas were mounted with Fluorsave reagent (Calbiochem). Confocal microscopy was performed on an Olympus FV1000 laser-scanning confocal microscope. Images were acquired sequentially, line by line, in order to reduce excitation and emission crosstalk, stepsize was defined according to the Nyquist-Shannon sampling theorem. Exposure settings that minimized oversaturated pixels in the final images were used. Twelve bit Images were then processed with FIJI, Z-sections were projected on a single plane using maximum intensity under Z-project function and finally converted to 8-bit RGB color mode.

Data Analysis

Results are expressed as mean±Standard Error of the Mean (SEM). Confocal stacks of 50 images were taken with the same settings. These images were Z projected and the fluorescence area was quantified with Fiji (Fiji Is Just ImageJ) software. Fluorescence data were then analysed using Mann Whitney U test with Prism 5 (GraphPad Software, San Diego, Calif.). p values <0.05 accepted as statistically significant.

Results

ShH10-GFP Targets Müller Glial Cells in the Wild-Type Mouse Retina

Previously, the AAV variant ShH10, engineered for specific glial transduction by directed evolution, has been characterized in rat retinas (Klimczak et al. 2009) and has been shown to transduce almost exclusively the Müller cells with small amount of off target expression in RGCs. To validate the Müller cell specificity of this virus in mouse retina, we injected intravitreally $1-4.10^{11}$ vg of ShH10 coding GFP under the control of a ubiquitous promoter. Injections were done in 7-week-old mice and followed weekly by in vivo fluorescence imaging up to 4 weeks after injection. We observed that GFP expression peaked at day 7 and remained constant thereafter. Histological examination of GFP expression in retinal flatmounts revealed a strong expression pattern localized near major vasculature and the optic nerve. Confocal imaging of retinal cross-sections and retinal flatmounts after GFAP immunostaining, showed exclusive Müller cell transduction using ShH10 and no GFP expression in astrocytes or retinal ganglion cells (RGCs). In conclusion, in wild-type mice ShH10-GFP is highly selective for Müller cells.

Müller Cell Transduction with ShH10-GFP in the Dp71-Null Mouse Retina

To assess Müller cell morphology in the Dp71-null mice, ShH10-GFP was delivered at an equal titer into the vitreous of Dp71-null mice. Transduction patterns were compared to wild-type retinas, by scanning laser ophthalmoscope (SLO) 15 days post-injection. One month post-injection in flat-mounted retinas were imaged and contrasted. Dp71-null mice show a more widespread and higher intensity Müller cell transduction compared to wild-type mice (n=6). Using these confocal stacks acquired using the same settings, we compared the transduction levels in the Müller cells by quantifying the extent of GFP labelled area and GFP intensity for each retina. The fluorescence area was approximately 2 fold larger in the Dp71-null than in the wild-type mice and the fluorescence intensity was approximately 6 fold higher in the Dp71-null than in the wild-type mice. Interactions between GFP labelled Müller glia and astrocytes were examined using higher magnification confocal images following GFAP labelling. This showed that ShH10 did not transduce any astrocytes and similar interactions were observed between astrocytes and blood vessels in both retinas. We also confirmed the high selectivity of ShH10 for Müller cells on agarose sections in Dp71-null mice showing there is no expression in other cell-types using ShH10. These results collectively show that the Müller cells can be more easily and intensively transduced by ShH10 in absence of Dp71. Furthermore, labelling of the Müller cells shows their endfeet are more spread out in absence of Dp71 than those of wild-type mice, confirming previous observations (Fort et al. 2008).

The Inner-Limiting Membrane is Altered in the Dp71-Null Mice

The Müller cell endfeet are deformed in absence of Dp71 (Fort et al. 2008), and this might contribute to changes in the structure of the inner limiting membrane (ILM) in addition to the previously described leakiness of the BRB. To compare the characteristics of the ILM in wild-type and Dp71-null mice, cross sections of Dp71-null retinas with GFP labelled Müller cells were examined in relation to the ILM. The ILM was labelled with an anti-laminin antibody because laminin is one of the ten extracellular matrix proteins secreted by Müller cell endfeet with nidogen 1 and 2, collagen 4, perlecan, collagen 18 and agrin (Halfter et al. 2008) constituting the ILM. The ILM and all layers of Dp71-null mouse retinas were thinner than those of the wild-type mice. The ILM and the rest of the retinal architecture are altered in absence of Dp71 likely accounting for the improvement in the transduction efficiency of the retina by AAV. We wanted to confirm our immunohistochemistry observations by in vivo OCT imaging. We used OCT imaging because it is the most reliable technique for obtaining in vivo measurement data without any chemical treatment of the tissue that could alter its structure. Thus, OCT imaging was performed 100 μm around the optic nerve on 8 eyes of each strain. Following measurements were made after Z projection of OCT images at 500 μm from the optic nerve: (i) the whole retina, from the retinal pigment epithelium (RPE) to the ganglion cell layer (GCL); (ii) the photoreceptor layer composed of the outer segments (OS) and the inner segments (IS); (iii) the outer nuclear layer (ONL); (iv) and the inner retina consisting of the inner nuclear layer (INL), the inner plexiform layer (IPL), the GCL and the ILM. After statistical analysis, we showed that each retinal cell layer is significantly thinner in Dp71-null mice than in wild-type mice. This observation confirms the results obtained by immunostaining of cryosections.

Intravitreal Injection of AAV5-GFP Strongly Transduces Photoreceptors in Dp71-Null Mouse Retina.

It has been shown that the mild digestion of the ILM with a nonspecific protease enhanced transduction of multiple retinal cell types from the vitreous, with AAV5 mediating particularly remarkable expression at the photoreceptor layer (Dalkara et al. 2009). AAV5 is known to only transduce the photoreceptor cells when it is injected subretinally or when the ILM of the retina is disrupted (Dalkara et al. 2009; Kolstad et al. 2010; Li et al. 2009). Based on this knowledge, we tested the ability of AAV5 to transduce retinal photoreceptors after injection into the vitreous of Dp71-null mice testing the hypothesis of a disrupted ILM. As anticipated, one month after intravitreal injection of AAV5-GFP, we obtained strong photoreceptor transduction across the entire retina in the Dp71-null mice whereas in the wild-type retina there was no detectable GFP expression. Agarose sections further confirm GFP expression restricted to the photoreceptor layer. The overall reduction in thickness of the retina might also contribute to this observation.

The Blood-Retinal Barrier of the Dp71-Null Mice is Not Permeable to AAVs

Knowing that in the Dp71-null mouse, the BRB is leaky to certain molecules as large as BSA, we wanted to test the extent of this permeability for particles, such as AAV. We checked if intravitreally injected ShH10-GFP can cross the BRB to go into the bloodstream. We collected blood from wild-type and Dp71-null mice 24, 48 and 72 hours after intravitreal injection of ShH10-GFP and measured the presence of viral DNA in the collected blood for each time point using PCR. We were not able to amplify GFP DNA from the bloodstream of either mouse strain indicating that the BRB is not permeable to virus when they are injected into the vitreous. As a positive control, AAV injected into the blood stream through the penile vein clearly showed presence of the GFP transgene in the circulation. This result is reassuring for the development of ocular gene therapy aimed at treating diseases showing a BRB breakdown.

DISCUSSION

Several retinal diseases are associated with a blood-retinal barrier breakdown phenotype and understanding the molecular mechanisms that contribute to the integrity of retinal barriers is of importance. The Dp71-null mouse is a good animal model to study the involvement of Müller glia in maintaining retinal barriers. Indeed, the absence of Dp71, most abundantly expressed in Müller glial cells, leads to the blood-retinal barrier breakdown in this mouse.

In order to understand the involvement of Müller glia in retinal permeability in the Dp71 mouse, we used an engineered AAV variant called ShH10 to label these cells. We then compared the interaction between Müller glia, retinal vasculature (BRB) and inner limiting membrane in the Dp71-null retina in comparison to a wild-type retina. ShH10 led to specific and efficient transgene expression in Müller glia, both in the Dp71-null and wild-type retinas. However the transduction patterns were found to be strikingly different in these two retinas. In the wild-type mouse, ShH10 led to intense and specific transduction of Müller cells in proximity to retinal blood vessels. It is well known that the ILM is thinner at the site of the major retinal blood vessels (Yanoff and Fine 1996), and the Müller glial endfeet wrap around the blood vessels which explain this typical transduction pattern alongside the major vasculature observed after intravitreal injection of AAV particles in a normal retina. Interestingly, in the Dp71-null mouse, ShH10 transduced a larger area of the retina, and led to stronger gene expression in the Müller cells. This reflects better viral access to Müller cell endfeet in the Dp71-null mouse. In absence of Dp71, the Müller cell endfeet are larger and more spread-out (Fort et al. 2008) presenting a larger contact surface for the virus at the ILM. Furthermore, the distribution of laminin, a major constituent of the ILM which normally binds α/β-dystroglycan (Claudepierre et al. 2000) is downregulated around the Müller cell endfeet as dystroglycan becomes dispersed through the glial cell body (Fort et al. 2008). All of these phenomena involving Müller cells and Dp71 likely contribute to the overall thinning of the retina in absence of Dp71 as well as to the thinning and permeabilization of the retinal barriers.

The thinning of the ILM is particularly important from a viral transduction standpoint as intravitreal administration of AAV vectors are hindered by the presence of this membrane (Dalkara et al. 2009; Ivanova et al. 2010; Yin et al. 2011). Intravitreal administration route is a preferred administration route to access the retina as it is non-invasive and leads to pan-retinal delivery. Current gene delivery methods require an injurious subretinal injection to reach the outer retina and only transduce a fraction of the retina (Jacobson et al. 2012). There have been several studies shedding light onto how ILM acts as a barrier to retinal transduction by AAVs (Aartsen et al. 2010; Cehajic-Kapetanovic et al. 2011; Dalkara et al. 2009; Kolstad et al. 2010). Previously it has been shown that mild digestion of the ILM with a non-specific protease, increases viral access to the retina (Dalkara et al. 2009). Similarly, it has been demonstrated (Aartsen et al. 2010) that Müller glial cell transduction by AAV6, an AAV serotype similar to ShH10, is improved by a disruption of the ILM by collagenase treatment. In this ladder study, the pattern of GFP expression follows the major vessels in the wild-type retina whereas GFP expression increases throughout the retina after mild-digestion of the ILM with collagenase, similar to our observations in the Dp71-null retina. In parallel, it has been shown that retinal degenerative disease can cause the ILM to become compromised providing better access to viral particles (Kolstad et al. 2010). Altogether these findings led us to hypothesize that the absence of Dp71 might lead to a more permissive ILM. Since the selective visualization of the ILM is challenging, we tested the hypothesis of a leaky ILM by applying another AAV serotype, which cannot transduce retinal cells across an intact ILM. AAV serotype 5, is able to transduce the retinal photoreceptors when applied subretinally yet it does not lead to retinal transduction when applied into the vitreous of wild-type rodents as its primary attachment receptors are shielded by the ILM and inner neurons. We observed that AAV5 leads to pan-retinal photoreceptor transduction in the Dp71-null mouse confirming that the ILM of this mouse strain is permissive allowing deeper retinal access to this serotype. As a perspective, we can imagine that transient inhibition of Dp71 via siRNA is a promising way to increase photoreceptor transduction allowing AAVs such as AAV5 to be delivered through the vitreous.

Dp71 expression is down-regulated after retinal detachment, proving the key role of this protein in the maintenance of a normal BRB permeability. Thus, Dp71 expression can potentially restore the barrier properties of the Müller cell endfeet if we can provide the protein exogenously. In this context, this preliminary study of AAV mediated targeting of Müller glia sets the basis for developing retinal gene therapy aimed at restoring Dp71 expression in retinal disease with leaky BRB. A potential obstacle for the development of AAV gene therapy for eye diseases with compromised BRB is the leakage of virus into the bloodstream. We thus analyzed blood samples from mice intravitreally injected with ShH10-GFP to detect the presence of viral particles in the bloodstream. We found no evidence of the GFP transgene in the circulation of Dp71-null or wild-type mice after intravitreal administration of ShH10.

In conclusion, the ILM of Dp71-null mouse is thinner and more permeable to several AAV serotypes after intravitreal injection while the BRB of these mice remains selective for AAV particles. These findings are reassuring for the development of gene therapies for diseases with compromised BRB and the Dp71-null mouse offers a good model for the study of pathologies showing a BRB breakdown such as AMD, diabetic retinopathy and the MacTel 2.

REFERENCES

Throughout this application, various references describe the state of the art to which this invention pertains. The disclosures of these references are hereby incorporated by reference into the present disclosure.

Aartsen W M, van Cleef K W, Pellissier L P, Hoek R M, Vos R M, Blits B, Ehlert E M, Balaggan K S, Ali R R, Verhaagen J and others. 2010. GFAP-driven GFP expression in activated mouse Muller glial cells aligning retinal blood vessels following intravitreal injection of AAV2/6 vectors. PLoS One 5(8):e12387.

Aurnhammer C, Haase M, Muether N, Hausl M, Rauschhuber C, Huber I, Nitschko H, Busch U, Sing A, Ehrhardt A and others. 2012. Universal real-time PCR for the detection and quantification of adeno-associated virus serotype 2-derived inverted terminal repeat sequences. Hum Gene Ther Methods 23(1):18-28.

Bainbridge J W, Smith A J, Barker S S, Robbie S, Henderson R, Balaggan K, Viswanathan A, Holder G E, Stockman A, Tyler N and others. 2008. Effect of gene therapy on visual function in Leber's congenital amaurosis. N Engl J Med 358(21):2231-9.

Cehajic-Kapetanovic J, Le Goff M M, Allen A, Lucas R J, Bishop P N. 2011. Glycosidic enzymes enhance retinal transduction following intravitreal delivery of AAV2. Mol Vis 17:1771-83.

Choi V W, Asokan A, Haberman R A, Samulski R J. 2007a. Production of recombinant adeno-associated viral vectors. Curr Protoc Hum Genet Chapter 12: Unit 12 9.

Choi V W, Asokan A, Haberman R A, Samulski R J. 2007b. Production of recombinant adeno-associated viral vectors for in vitro and in vivo use. Curr Protoc Mol Biol Chapter 16: Unit 16 25.

Cideciyan A V, Aleman T S, Boye S L, Schwartz S B, Kaushal S, Roman A J, Pang J J, Sumaroka A, Windsor E A, Wilson J M and others. 2008. Human gene therapy for RPE65 isomerase deficiency activates the retinoid cycle of vision but with slow rod kinetics. Proc Natl Acad Sci USA 105(39):15112-7.

Claudepierre T, Mornet D, Pannicke T, Forster V, Dalloz C, Bolanos F, Sahel J, Reichenbach A, Rendon A. 2000. Expression of Dp71 in Muller glial cells: a comparison with utrophin- and dystrophin-associated proteins. Invest Ophthalmol Vis Sci 41(1):294-304.

Dalkara D, Kolstad K D, Caporale N, Visel M, Klimczak R R, Schaffer D V, Flannery J G. 2009. Inner limiting membrane barriers to AAV-mediated retinal transduction from the vitreous. Mol Ther 17(12):2096-102.

Fort P E, Sene A, Pannicke T, Roux M J, Forster V, Mornet D, Nudel U, Yaffe D, Reichenbach A, Sahel J A and others. 2008. Kir4.1 and AQP4 associate with Dp71- and utrophin-DAPs complexes in specific and defined microdomains of Muller retinal glial cell membrane. Glia 56(6):597-610.

Halfter W, Dong S, Dong A, Eller A W, Nischt R. 2008. Origin and turnover of ECM proteins from the inner limiting membrane and vitreous body. Eye (Lond) 22(10):1207-13.

Hosoya K, Tachikawa M. 2012. The inner blood-retinal barrier: molecular structure and transport biology. Adv Exp Med Biol 763:85-104.

Ivanova E, Hwang G S, Pan Z H, Troilo D. 2010. Evaluation of AAV-mediated expression of Chop2-GFP in the marmoset retina. Invest Ophthalmol Vis Sci 51(10):5288-96.

Jacobson S G, Cideciyan A V, Ratnakaram R, Heon E, Schwartz S B, Roman A J, Peden M C, Aleman T S, Boye S L, Sumaroka A and others. 2012. Gene therapy for leber congenital amaurosis caused by RPE65 mutations: safety and efficacy in 15 children and adults followed up to 3 years. Arch Ophthalmol 130(1):9-24.

Klimczak R R, Koerber J T, Dalkara D, Flannery J G, Schaffer D V. 2009. A novel adeno-associated viral variant for efficient and selective intravitreal transduction of rat Muller cells. PLoS One 4(10):e7467.

Kolstad K D, Dalkara D, Guerin K, Visel M, Hoffmann N, Schaffer D V, Flannery J G. 2010. Changes in adeno-associated virus-mediated gene delivery in retinal degeneration. Hum Gene Ther 21(5):571-8.

Li W, Kong F, Li X, Dai X, Liu X, Zheng Q, Wu R, Zhou X, Lu F, Chang B and others. 2009. Gene therapy following subretinal AAV5 vector delivery is not affected by a previous intravitreal AAV5 vector administration in the partner eye. Mol Vis 15:267-75.

Maguire A M, Simonelli F, Pierce E A, Pugh E N, Jr., Mingozzi F, Bennicelli J, Banfi S, Marshall K A, Testa F, Surace E M and others. 2008. Safety and efficacy of gene transfer for Leber's congenital amaurosis. N Engl J Med 358(21):2240-8.

Sarig R, Mezger-Lallemand V, Gitelman I, Davis C, Fuchs O, Yaffe D, Nudel U. 1999. Targeted inactivation of Dp71, the major non-muscle product of the DMD gene: differential activity of the Dp71 promoter during development. Hum Mol Genet 8(1):1-10.

Sene A, Tadayoni R, Pannicke T, Wurm A, El Mathari B, Benard R, Roux M J, Yaffe D, Mornet D, Reichenbach A and others. 2009. Functional implication of Dp71 in osmoregulation and vascular permeability of the retina. PLoS One 4(10):e7329.

Shen W, Fruttiger M, Zhu L, Chung S H, Barnett N L, Kirk J K, Lee S, Coorey N J, Killingsworth M, Sherman L S and others. 2012. Conditional Muller cell ablation causes independent neuronal and vascular pathologies in a novel transgenic model. J Neurosci 32(45):15715-27.

Tadayoni R, Rendon A, Soria-Jasso L E, Cisneros B. 2012. Dystrophin Dp71: the smallest but multifunctional product of the Duchenne muscular dystrophy gene. Mol Neurobiol 45(1):43-60.

Yanoff M, Fine B S. 1996. Occular Pathology: Mosby-Wolfe.

Yin L, Greenberg K, Hunter J J, Dalkara D, Kolstad K D, Masella B D, Wolfe R, Visel M, Stone D, Libby R T and others. 2011. Intravitreal injection of AAV2 transduces macaque inner retina. Invest Ophthalmol Vis Sci 52(5):2775-83.

The invention claimed is:

1. A method for enhancing delivery of a polynucleotide of interest in the retina of a subject affected with or likely to be affected with a retinal disease comprising the step of injecting into the vitreous of said subject an amount of a vector containing the polynucleotide of interest in combination with an amount of an inhibitor of Dp71 expression, wherein the inhibitor of Dp71 expression is a siRNA.

2. The method of claim 1 wherein the retinal disease is an inherited retinal disease or an acquired retinal disease.

3. The method of claim 2 wherein the acquired retinal disease is a macular degeneration such as age related macular degeneration, or diabetic retinopathy.

4. The method of claim 2 wherein the inherited retinal disease is selected from the group consisting of Bardet-Biedl syndrome; Bassen-Kornzweig syndrome, Best disease, choroidema, gyrate atrophy, Leber congenital amaurosis, Refsun syndrome, Stargardt disease; Cone or cone-rod dystrophy; Congenital stationary night blindness; Macular degeneration; Optic atrophy; Retinitis pigmentosa; Syndromic or systemic retinopathy; and Usher syndrome.

5. The method of claim 1 wherein a product encoded by the polynucleotide of interest is a polypeptide that enhances the function of retinal cells selected from the group consisting of rod or cone photoreceptor cells, retinal ganglion cells, Muller cells, bipolar cells, amacrine cells, horizontal cells, and retinal pigmented epithelial cells.

6. The method of claim 5 wherein the product encoded by the polynucleotide of interest is selected from the group consisting of a neuroprotective polypeptide, an anti-angiogenic polypeptide, and a neurotrophic factor.

7. The method of claim 1 wherein a product encoded by the polynucleotide of interest is a site-specific endonuclease.

8. The method of claim 1 wherein the vector is a recombinant adeno-associated virus (AAV).

9. The method of claim 8 wherein the AAV is selected from the group consisting of AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), and AAV type 8 (AAV-8) and AAV type 9 (AAV9).

10. The method of claim 1 wherein the vector is a pseudotyped AAV vector.

11. The method of claim 10 wherein the pseudotyped AAV vector is selected from the group consisting of AAV2/5, AAV2/6, and AAV2/8.

12. The method of claim 1 wherein the vector is AAV engineered vector having a mutated capsid.

13. The method of claim 1 wherein the vector is a AAV engineered vector comprising a variant AAV capsid protein, wherein the variant AAV capsid protein comprises an insertion of from about 5 amino acids to about 11 amino acids in the capsid protein GH loop relative to a corresponding parental AAV capsid protein, and wherein the variant capsid protein confers increased infectivity of a retinal cell compared to the infectivity of the retinal cell by an AAV virion comprising the corresponding parental AAV capsid protein.

14. The method of claim 1 wherein the vector and the inhibitor of Dp71 expression are injected simultaneously or sequentially into the vitreous of the subject.

15. A method for treating a retinal disease in a subject in need thereof, comprising enhancing delivery of a polynucleotide of interest in the retina of the subject by injecting into the vitreous of the subject a therapeutically effective dose of a vector containing the polynucleotide of interest in combination with a therapeutically effective dose of an inhibitor of Dp71 expression, wherein the therapeutic doses are sufficient to treat the retinal disease in the subject and wherein the inhibitor of Dp71 expression is a siRNA.

16. The method of claim 7, wherein the site-specific endonuclease is TALEnuclease, meganuclease or Zinc finger nuclease.

17. The method of claim 12, wherein the mutated capsid is a tyrosine mutated capsid.

\* \* \* \* \*